United States Patent
Ando et al.

(10) Patent No.: US 8,329,816 B2
(45) Date of Patent: Dec. 11, 2012

(54) SILICONE MICROEMULSION COMPOSITION

(75) Inventors: Yuji Ando, Annaka (JP); Motohiko Hirai, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/448,651

(22) Filed: Apr. 17, 2012

(65) Prior Publication Data

US 2012/0270985 A1    Oct. 25, 2012

(30) Foreign Application Priority Data

Apr. 22, 2011 (JP) ................. 2011-095684

(51) Int. Cl.
*C08K 3/00*    (2006.01)
(52) U.S. Cl. ............ 524/588; 424/401; 424/70.12; 516/55; 516/53
(58) Field of Classification Search .......... 524/588; 424/401, 70.12; 516/53, 55
See application file for complete search history.

(56) References Cited

U.S. PATENT DOCUMENTS

| | | | | |
|---|---|---|---|---|
| 4,359,545 A | * | 11/1982 | Ona et al. | 252/8.61 |
| 4,366,001 A | * | 12/1982 | Ona et al. | 106/287.11 |
| 4,427,815 A | * | 1/1984 | Ona et al. | 252/8.61 |
| 4,744,978 A | * | 5/1988 | Homan et al. | 424/70.12 |
| 4,857,212 A | | 8/1989 | Ona et al. | |
| 5,063,044 A | * | 11/1991 | Kohl et al. | 424/70.12 |
| 5,280,019 A | * | 1/1994 | Klimisch | 514/63 |
| 5,851,431 A | * | 12/1998 | Ishikawa et al. | 516/74 |
| 6,290,942 B1 | * | 9/2001 | Nakazato et al. | 424/70.121 |
| 2006/0210506 A1 | | 9/2006 | Kamei et al. | |
| 2012/0010169 A1 | | 1/2012 | Teshigawara et al. | |

FOREIGN PATENT DOCUMENTS

| | | |
|---|---|---|
| JP | 63-270875 | 11/1988 |
| JP | 2-284959 | 11/1990 |
| JP | 4338648 | 7/2009 |
| WO | 2010/110047 A1 | 9/2010 |

* cited by examiner

*Primary Examiner* — Margaret Moore

(74) *Attorney, Agent, or Firm* — Oblon, Spivak, McClelland, Maier & Neustadt, L.L.P.

(57) ABSTRACT

A silicone microemulsion composition obtained by microemulsifying a carboxy-modified organopolysiloxane, and having a lower surface tension than conventional microemulsions. The composition includes 100 parts by mass of a specific carboxy-modified organopolysiloxane (A), 25 to 75 parts by mass of a specific polyether-modified organopolysiloxane (B), 0.1 to 10 parts by mass of an anionic surfactant, and 20 to 6,000 parts by mass of water, wherein the average particle size of the emulsion particles is not more than 100 nm.

5 Claims, No Drawings

SILICONE MICROEMULSION COMPOSITION

BACKGROUND OF THE INVENTION

1. Field of the Invention

The present invention relates to a stable silicone microemulsion composition obtained from a carboxy-modified organopolysiloxane using a silicone-based nonionic surfactant. This silicone microemulsion composition can be used in cosmetic materials and household products.

2. Description of the Prior Art

Examples of conventionally known silicone microemulsions include amino silicone microemulsions obtained from amino group-containing organopolysiloxanes using a nonionic surfactant and an organic acid. The average particle size within these microemulsions is 100 nm or less, which is extremely small compared with the average particle size of macroemulsions (which exceed 100 nm). These amino silicone microemulsions exhibit excellent emulsion stability, excellent shear stability when used in diluted form, and superior adsorption to substrates, and are therefore used within a wide range of industrial fields, as fiber treatment agents, release agents, water repellent agents and hair cosmetic materials and the like (Patent Document 1).

Techniques for obtaining microemulsions from organopolysiloxanes other than amino group-containing organopolysiloxanes are now being investigated. For example, a hair cosmetic material that exhibits superior adhesion to hair, comprising an organopolysiloxane having carboxyl groups within a portion of a dimethylpolysiloxane chain and a surfactant has been proposed (Patent Document 2). Further, the use of a microemulsion with an average particle size of not more than 150 nm, obtained from a carboxy-modified organopolysiloxane using a nonionic surfactant and/or an anionic surfactant, as the main agent within a fiber treatment agent has also been proposed (Patent Document 3). Moreover, a solubilized composition obtained by solubilizing a carboxy-modified organopolysiloxane with a branched polyoxyethylene alkyl ether-type nonionic surfactant has also been proposed (Patent Document 4).

Patent Document 1: JP 02-284959 A
Patent Document 2: JP 4,338,648 B
Patent Document 3: JP 63-270875 A
Patent Document 4: WO 2010/110047

SUMMARY OF THE INVENTION

However, conventional silicone microemulsions are all obtained using alkyl-type nonionic surfactants, but satisfactorily lowering the surface tension of such silicone microemulsions is not an easy task. In those cases where the silicone microemulsion is used in an application such as a cosmetic material or a household product, a lower surface tension ensures improved wettability of the material being treated, enabling a more efficient treatment of the surface of the material.

The present invention has been developed in light of these types of issues associated with the conventional technology, and has an object of providing a silicone microemulsion composition that is obtained by microemulsifying a carboxy-modified organopolysiloxane and exhibits a lower surface tension than conventional microemulsions.

The inventors of the present invention discovered that by microemulsifying a carboxy-modified organopolysiloxane using a silicone-based nonionic surfactant instead of an alkyl-type nonionic surfactant, a silicone microemulsion composition having a lower surface tension than conventional microemulsions could be obtained, and they were therefore able to complete the present invention.

In other words, the present invention provides a silicone microemulsion composition comprising:

(A) 100 parts by mass of a carboxy-modified organopolysiloxane represented by a general formula [1] shown below, $$R^2-(R^1{}_2SiO)_m(R^2R^1SiO)_nR^1{}_2Si-R^2 \quad [1]$$

wherein each $R^1$ independently represents an unsubstituted or substituted monovalent hydrocarbon group of 1 to 20 carbon atoms, each $R^2$ independently represents $R^1$ or $-R^3COOH$, provided that at least one $R^2$ group represents $-R^3COOH$, $R^3$ represents a divalent hydrocarbon group, m represents a number of 50 to 1,000 and n represents a number of 0 to 20;

(B) 25 to 75 parts by mass of a polyether-modified organopolysiloxane represented by a general formula [2] shown below, $$R^4-(R^1{}_2SiO)_o(R^4R^1SiO)_pR^1{}_2Si-R^4 \quad [2]$$

wherein $R^1$ is as defined above, each $R^4$ independently represents $R^1$ or $-(CH_2)_aO(C_2H_4O)_b(C_3H_6O)_cR^5$, provided that at least one $R^4$ group represents $-(CH_2)_aO(C_2H_4O)_b(C_3H_6O)_cR^5$, $R^5$ represents a hydrogen atom, a hydrocarbon group of 1 to 20 carbon atoms or $-(CO)-R^6$, $R^6$ represents a hydrocarbon group of 1 to 10 carbon atoms, o represents a number of 0 to 3, p represents a number of 1 to 3, a represents a number of 2 to 5, b represents a number of 5 to 15, and c represents a number of 0 to 10;

(C) 0.1 to 10 parts by mass of an anionic surfactant; and
(D) water; wherein
the average particle size of the emulsion particles is not more than 100 nm.

In one embodiment of the present invention, the silicone microemulsion composition of the present invention further comprises a base as a component (E). In another embodiment, the silicone microemulsion composition of the present invention further comprises a polyhydric alcohol as a component (F). In yet another embodiment, a dilute system composed of more than 0% by mass but not more than 10% by mass of the silicone microemulsion composition of the present invention, with the remainder being water, exhibits a surface tension of not more than 30 mN/m.

The silicone microemulsion composition of the present invention is obtained by using the polyether-modified organopolysiloxane of the component (B) as a silicone-based nonionic surfactant to microemulsify the carboxy-modified organopolysiloxane. The silicone microemulsion composition exhibits excellent light transmittance, is very fine and stable, and has a lower surface tension than conventional silicone microemulsion compositions obtained using alkyl-type nonionic surfactants.

DETAILED DESCRIPTION OF THE PREFERRED EMBODIMENTS

A more detailed description of the present invention is presented below. In this description, the term "average particle size" refers to the size where the volume-based cumulative distribution reaches 50%, and is measured using a dynamic light scattering method.

[Component (A)]

The component (A) is a carboxy-modified organopolysiloxane represented by a general formula [1] shown below. The component (A) may be a single compound or a combination of two or more compounds.

$$R^2-(R^1{}_2SiO)_m(R^2R^1SiO)_nR^1{}_2Si-R^2 \quad [1]$$

In the formula [1], each $R^1$ independently represents an unsubstituted or substituted monovalent hydrocarbon group of 1 to 20 carbon atoms, each $R^2$ independently represents $R^1$ or —$R^3$COOH, provided that at least one $R^2$ group represents —$R^3$COOH, $R^3$ represents a divalent hydrocarbon group, m represents a number of 50 to 1,000 and n represents a number of 0 to 20.

Each $R^1$ group preferably independently represents an unsubstituted or substituted monovalent hydrocarbon group of 1 to 6 carbon atoms. Examples of $R^1$ include unsubstituted or substituted alkyl groups of 1 to 20 carbon atoms, unsubstituted or substituted cycloalkyl groups of 3 to 20 carbon atoms, unsubstituted or substituted alkenyl groups of 2 to 20 carbon atoms, unsubstituted or substituted aryl groups of 6 to 20 carbon atoms, and unsubstituted or substituted aralkyl groups of 7 to 20 carbon atoms. Specific examples of $R^1$ include alkyl groups such as a methyl group, ethyl group, propyl group, butyl group, pentyl group, hexyl group, heptyl group, octyl group, nonyl group, decyl group, dodecyl group, tetradecyl group, hexadecyl group and octadecyl group; cycloalkyl groups such as a cyclopentyl group and cyclohexyl group; alkenyl groups such as a vinyl group and allyl group; aryl groups such as a phenyl group, tolyl group and naphthyl group; aralkyl groups such as a benzyl group and phenethyl group; and groups in which some or all of the hydrogen atoms within one of the above hydrocarbon groups have each been substituted with a halogen atom (such as a fluorine atom, bromine atom or chlorine atom), a polar group (such as an amino group, acryloyloxy group, methacryloyloxy group, epoxy group or mercapto group) or a polar group-containing organic group. Of the above, a methyl group, ethyl group, propyl group, butyl group or phenyl group is preferred and 80 mol % or more of all the $R^1$ groups are preferably methyl groups.

$R^3$ preferably represents a divalent hydrocarbon group of 2 to 20 carbon atoms, and examples include groups represented by the formula: —$(CH_2)_x$—, wherein x represents an integer of 2 to 20.

There are no particular limitations on the number of carboxyl groups within the component (A), but the carboxyl equivalent weight for the component (A) is preferably within a range from 1,000 to 5,000 g/mol. m and n are numbers that satisfy the respective numerical ranges described above, and are preferably numbers that ensure that the carboxyl equivalent weight falls within the range from 1,000 to 5,000 g/mol.

[Component (B)]

The component (B) is a polyether-modified organopolysiloxane represented by a general formula [2] shown below. The component (B) may be a single compound or a combination of two or more compounds.

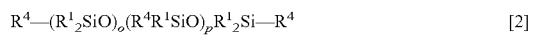

$$R^4-(R^1{}_2SiO)_o(R^4R^1SiO)_pR^1{}_2Si-R^4 \qquad [2]$$

In the formula [2], $R^1$ is as defined above, each $R^4$ independently represents $R^1$ or —$(CH_2)_aO(C_2H_4O)_b(C_3H_6O)_cR^5$, provided that at least one $R^4$ group represents —$(CH_2)_aO(C_2H_4O)_b(C_3H_6O)_cR^5$, and preferably that at least one of the $R^4$ groups not bonded to a terminal silicon atom represents —$(CH_2)_aO(C_2H_4O)_b(C_3H_6O)_cR^5$, $R^5$ represents a hydrogen atom, a hydrocarbon group of 1 to 20 carbon atoms or —(CO)—$R^6$, $R^6$ represents a hydrocarbon group of 1 to 10 carbon atoms, o represents a number of 0 to 3, p represents a number of 1 to 3, a represents a number of 2 to 5, b represents a number of 5 to 15, and c represents a number of 0 to 10.

Specific examples of the hydrocarbon group of 1 to 20 carbon atoms represented by $R^5$ include the same groups as those listed above for $R^1$. Examples of $R^6$ include alkyl groups of 1 to 10 carbon atoms, cycloalkyl groups of 3 to 10 carbon atoms, alkenyl groups of 2 to 10 carbon atoms, aryl groups of 6 to 10 carbon atoms, and aralkyl groups of 7 to 10 carbon atoms. Specific examples of $R^6$ include alkyl groups such as a methyl group, ethyl group, propyl group, butyl group, pentyl group, hexyl group, heptyl group, octyl group, nonyl group and decyl group; cycloalkyl groups such as a cyclopentyl group and cyclohexyl group; alkenyl groups such as a vinyl group and allyl group; aryl groups such as a phenyl group, tolyl group and naphthyl group; and aralkyl groups such as a benzyl group and phenethyl group. $R^5$ is preferably a hydrogen atom, methyl group, ethyl group, propyl group, butyl group or acetyl group, and is more preferably a hydrogen atom or a methyl group.

The HLB value of the component (B) varies depending on the values of o, p, a, b and c, but o, p, a, b and c are preferably numbers that satisfy the respective numerical ranges described above, and yield an HLB value for the component (B) within a range from 10 to 15.

In those cases where the polyoxyalkylene portions within the formula [2] are composed of both ethylene oxide units and propylene oxide units, these units may form either a block polymer or a random polymer.

[Component (C)]

The component (C) is an anionic surfactant. A single surfactant may be used alone, or two or more surfactants may be used in combination. Specific examples of the component (C) include diethanolamine N-acyl-L-glutamate, triethanolamine N-acyl-L-glutamate, sodium N-acyl-L-glutamate, sodium alkane sulfonate, ammonium alkyl (12,14,16) sulfate, triethanolamine alkyl (11,13,15) sulfate, triethanolamine alkyl (12 to 14) sulfate, triethanolamine alkyl sulfate solution, sodium alkyl (12,13) sulfate, sodium alkyl sulfate solution, sodium isethionate, sodium isostearyl lactate, disodium undecylenoylamidoethyl sulfosuccinate, triethanolamine oleyl sulfate, sodium oleyl sulfate, disodium oleamido sulfosuccinate, potassium oleate, sodium oleate, morpholine oleate, oleyl sarcosine, sodium methyl oleoyl taurate, potassium-containing soap base, potassium soap base solution, potassium soap, carboxylated polyoxyethylene tridodecyl ether, sodium polyoxyethylene tridodecyl ether carboxylate (3 E.O.), triethanolamine N-hydrogenated tallow acyl-L-glutamate, sodium N-hydrogenated tallow acyl-L-glutamate, sodium hydrogenated coconut oil fatty acid glyceryl sulfate, sodium diundecylenoylamidoethyl sulfosuccinate, sodium stearyl sulfate, potassium stearate, triethanolamine stearate, sodium stearate, sodium N-stearoyl-L-glutamate, disodium stearoyl-L-glutamate, sodium stearoyl methyl taurate, sodium dioctyl sulfosuccinate, sodium dioctyl sulfosuccinate solution, disodium polyoxyethylene monooleylamide sulfosuccinate solution (2 E.O.), disodium polyoxyethylene lauroylethanolamide sulfosuccinate solution (5 E.O.), disodium lauryl sulfosuccinate, diethanolamide cetyl sulfate, sodium cetyl sulfate, soap base, sodium cetostearyl sulfate, triethanolamine tridecyl sulfate, potassium palmitate, sodium palmitate, sodium palmitoyl methyl taurate, sodium ricinoleate solution (30% by mass), ammonium polyoxyethylene alkyl ether sulfate solution (3 E.O.), diethanolamine polyoxyethylene alkyl (12,13) ether sulfate solution (3 E.O.), triethanolamine polyoxyethylene alkyl ether sulfate solution (3 E.O.), triethanolamine polyoxyethylene alkyl (11,13,15) ether sulfate (1 E.O.), triethanolamine polyoxyethylene alkyl (12,13) ether sulfate (3 E.O.), sodium polyoxyethylene alkyl ether sulfate solution (3 E.O.), sodium polyoxyethylene alkyl (11,13,15) ether sulfate (1 E.O.), sodium polyoxyethylene alkyl (11 to 15) ether sulfate (3 E.O.), sodium polyoxyethylene alkyl (12,13) ether sulfate (3 E.O.), sodium polyoxyethylene alkyl (12 to 14) ether sulfate (3 E.O.), sodium polyoxyethylene alkyl (12 to 15) ether sulfate (3 E.O.), disodium polyoxyethylene alkyl (12 to 14) sulfosuccinate (7 E.O.), sodium polyoxyethylene undecyl ether sulfate, sodium polyoxyethylene octylphenyl ether sulfate solution, ammonium polyoxyethylene oleyl ether sulfate, disodium polyoxyethylene lauryl sulfosuccinate, sodium polyoxyethylene nonylphenyl ether sulfate, sodium polyoxyethylene pentadecyl ether sulfate, triethanolamine polyoxyethylene myristyl ether sulfate, sodium polyoxyethylene myristyl ether sulfate, sodium polyoxyethylene myristyl ether sulfate (3 E.O.), sodium polyoxyethylene lauryl ether acetate solution (16 E.O.), ammonium polyoxyethylene lauryl ether sulfate (2 E.O.), triethanolamine polyoxyethylene lauryl ether sulfate, sodium polyoxyethylene lauryl ether sulfate, diethanolamine myristyl sulfate, sodium myristyl sulfate, potassium myristate, sodium N-myristoyl-L-glutamate, sodium myristoyl methylaminoacetate, sodium myristoyl methyl-β-alanine solution, sodium myristoyl methyl taurate, medicinal soap, triethanolamine-magnesium coconut oil alkyl sulfate, triethanolamine N-coconut oil fatty acid acyl-L-glutamate, sodium N-coconut oil fatty acid acyl-L-glutamate, sodium coconut oil fatty acid-ethyl ester sulfonate, potassium cocoate, potassium cocoate solution, sodium N-coconut oil fatty acid-hydrogenated tallow acyl-L-glutamate, sarcosine cocoate, triethanolamine sarcosine cocoate, sodium sarcosine cocoate, triethanolamine cocoate, triethanolamine cocoate solution, sodium cocoate, sodium methyl alanine cocoate, sodium methyl alanine cocoate solution, potassium methyl taurine cocoate, sodium methyl taurine cocoate, sodium laurylaminodipropionate, sodium laurylaminodipropionate solution (30% by mass), sodium lauryl sulfoacetate, sodium lauryl benzenesulfonate, lauryl sulfuric acid, ammonium lauryl sulfate, potassium lauryl sulfate, diethanolamine lauryl sulfate, triethanolamine lauryl sulfate, sodium lauryl sulfate, magnesium lauryl sulfate, monoethanolamine lauryl sulfate, potassium laurate, triethanolamine laurate, triethanolamine laurate solution, sodium laurate, triethanolamine laurate myristate, triethanolamine lauroyl-L-glutamate, sodium N-lauroyl-L-glutamate, lauroyl sarcosine, potassium lauroyl sarcosine, triethanolamine lauroyl sarcosine solution, sodium lauroyl sarcosine, sodium lauroyl methyl-β-alanine solution, sodium lauroyl methyl taurate, and sodium lauroyl methyl taurate solution. The numbers appended to the term "alkyl" in some of the above compound names refer to the number of carbon atoms within that alkyl group. For example, "ammonium alkyl (12,14,16) sulfate" refers to ammonium $C_{1-2}$-alkyl sulfate, ammonium $C_{1-4}$-alkyl sulfate or ammonium $C_{1-6}$-alkyl sulfate.

[Component (D)]

The component (D) is water. Examples of the component (D) include purified waters such as ion-exchanged water, distilled water and deionized water.

[Component (E)]

The component (E) is a base, which may be added to the silicone microemulsion composition of the present invention as an optional component. A single base may be used alone as the component (E), or two or more bases may be used in combination. Specific examples of the component (E) include diammonium hydrogen phosphate, disodium hydrogen phosphate, dipotassium hydrogen phosphate, ammonium dihydrogen phosphate, sodium dihydrogen phosphate, potassium dihydrogen phosphate, trisodium phosphate, tripotassium phosphate, ammonium acetate, sodium acetate, potassium acetate, sodium citrate, diammonium citrate, sodium carbonate, potassium carbonate, ammonium carbonate, sodium hydrogen carbonate, ammonium hydrogen carbonate, sodium hydroxide, potassium hydroxide, ammonia and triethanolamine.

[Component (F)]

The component (F) is a polyhydric alcohol, namely a compound having two or more hydroxyl groups within each molecule, and may be added to the silicone microemulsion composition of the present invention as an optional component. A single compound may be used alone as the component (F), or two or more compounds may be used in combination. Specific examples of the component (F) include aliphatic acyclic diols such as ethylene glycol, 1,2-propylene glycol, 1,3-propylene glycol, dipropylene glycol, 1,2-butanediol, 1,3-butanediol, 1,4-butanediol, 2,3-butanediol, 1,5-pentanediol, 2-methyl-2,4-pentanediol, 1,6-hexanediol, polyethylene glycol and polypropylene glycol; alicyclic diols such as 1,2-cyclohexanediol, 1,3-cyclohexanediol, 1,4-cyclohexanediol and 1,2-di(hydroxymethyl)cyclohexanone; aromatic diols such as 1,2-di(hydroxymethyl)benzene; and polyols containing three or more hydroxyl groups within each molecule, including alkane polyols such as pentaerythritol and glycerol, sugar derivatives such as sorbitol and mannitol, and polyalkane polyols such as polyglycerol (such as pentaglycerol and hexaglycerol) and polypentaerythritol.

The silicone microemulsion composition of the present invention comprises 100 parts by mass of the carboxy-modified organopolysiloxane of the component (A), 25 to 75 parts by mass of the polyether-modified organopolysiloxane of the component (B), 0.1 to 10 parts by mass of the anionic surfactant of the component (C), and 20 to 6,000 parts by mass of the water of the component (D).

In order to ensure that the special features of the microemulsion and the carboxy-modified organopolysiloxane are not lost, the amount of the component (B) is typically within a range from 25 to 75 parts by mass, and preferably from 45 to 55 parts by mass, per 100 parts by mass of the component (A).

From the viewpoints of improving the stability of the emulsion and preventing any increase in the surface tension, the amount of the component (C) is typically within a range from 0.1 to 10 parts by mass, and preferably from 1 to 3 parts by mass, per 100 parts by mass of the component (A).

The amount of the component (D) is typically within a range from 20 to 6,000 parts by mass, preferably from 23 to 6,000 parts by mass, and more preferably from 48 to 6,000 parts by mass, per 100 parts by mass of the component (A).

The base of the component (E) has the effect of increasing the viscosity of the emulsion, whereas the polyhydric alcohol of the component (F) has the effect of lowering the viscosity of the emulsion. The viscosity of the silicone microemulsion composition of the present invention can be adjusted by using either one of the component (E) and the component (F), whereas using the component (E) and the component (F) in combination facilitates the preparation of an emulsion of any arbitrary viscosity. The amount of the component (E) is preferably sufficient to provide 0.1 to 1.0 molar equivalents of the base of the component (E) per 1 molar equivalent of carboxyl groups within the component (A). This type of amount can typically be realized by using an amount of the component (E) within a range from 0 to 5 parts by mass, preferably from 1 to 4 parts by mass, and still more preferably from 1 to 3 parts by mass, per 100 parts by mass of the component (A). The amount of the component (F) is preferably within a range from 0 to 10 parts by mass, more preferably from 0.5 to 8 parts by mass, and still more preferably from 0.5 to 2 parts by mass, per 100 parts by mass of the component (A).

The silicone microemulsion composition of the present invention can be prepared by uniformly mixing the components (A) to (D), and in some cases the components (E) and/or (F), using an emulsification apparatus such as Homomixer, Colloidmill, Line mixer, a universal mixing machine, Ultra mixer, Planetary mixer or Combi mix. All of the components may be mixed simultaneously, or alternatively, all of the components other than the component (D) may first be mixed with a portion of the component (D) (phase inversion water) in a phase inversion step, with the remainder of the component (D) (dilution water) then being added and mixed in a subsequent dilution step.

The average particle size of the emulsion particles within the silicone microemulsion composition of the present invention is typically not more than 100 nm, and is preferably within a range from 10 to 80 nm.

The surface tension of a dilute system composed of more than 0% by mass but not more than 10% by mass of the silicone microemulsion composition of the present invention, with the remainder being water, is typically not more than 30 mN/m, and is preferably within a range from 20 to 27 mN/m.

EXAMPLES

Specifics of the present invention are described below using a series of examples and comparative examples, but the present invention is in no way limited by these examples. In the following examples, "parts" refers to parts by mass, and "Me" represents a methyl group. Ion-exchanged water was used as the water. The average particle size was measured using a dynamic light scattering particle size distribution analyzer "N4 Plus Submicron Particle Size Analyzer" manufactured by Beckman Coulter, Inc., the light transmittance was measured using an ultraviolet-visible spectrophotometer UV-1800 (measurement wavelength: 500 nm) manufactured by Shimadzu Corporation, and the surface tension was measured using an automated surface tension meter "Face" (model number: CBVP-Z) manufactured by Kyowa Interface Science Co. Ltd. The external appearance was evaluated by visual inspection. Further, the viscosity was measured at 25° C. using a rotational viscometer. The average composition formulas of the organopolysiloxanes are reported using the following symbol abbreviations.

M: $(CH_3)_3SiO_{1/2}$
D: $(CH_3)_2SiO_{2/2}$
$D^R$: $(R)(CH_3)SiO_{2/2}$

Example 1

To 50 parts of a carboxy-modified organopolysiloxane (average composition formula: $M_2D_{280}D^R{}_{16}$, wherein R represents —$(CH_2)_{10}COOH$, carboxyl equivalent weight: 3,960 g/mol) were added and mixed 25 parts of a polyether-modified organopolysiloxane A (average composition formula: $M_2D^R$, wherein R represents —$(CH_2)_3O(C_2H_4O)_8Me$), 1 part of an anionic surfactant (product name: Emal 20C, manufactured by Kao Corporation) and 10 parts of phase inversion water, and following mixing, a further 14 parts of dilution water were added and mixed uniformly, yielding a silicone microemulsion composition. The thus obtained silicone microemulsion composition had an average particle size for the emulsion particles of 36 nm, and a viscosity of 5,060 mPa·s. To 100 parts of this silicone microemulsion composition were added 4,900 parts of water, thus preparing a dilute system composed of 2% by mass of the composition, with the remainder being water (concentration of the aforementioned carboxy-modified organopolysiloxane: 1% by mass). As shown in Table 1, this dilute system had a light transmittance of 89.6%, an average particle size for the emulsion particles of 31 nm, and a surface tension of 23.2 mN/m. Even when the dilute system was left to stand for one month at room temperature, no change in external appearance was observed.

Example 2

With the exceptions of also adding 1.88 parts of a base (triethanolamine) (an amount sufficient to provide 1 molar equivalent of the base per 1 molar equivalent of carboxyl groups within the carboxy-modified organopolysiloxane) to the carboxy-modified organopolysiloxane of the example 1, and altering the amount of the dilution water from 14 parts to 12.12 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 3

With the exceptions of also adding 3 parts of a polyhydric alcohol (1,3-butanediol) to the carboxy-modified organopolysiloxane of the example 1, and altering the amount of the dilution water from 14 parts to 11 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 4

With the exceptions of also adding 1.88 parts of a base (triethanolamine) and 3 parts of a polyhydric alcohol (1,3-butanediol) to the carboxy-modified organopolysiloxane of the example 1, and altering the amount of the dilution water from 14 parts to 9.12 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 5

With the exceptions of altering the amount of the polyether-modified organopolysiloxane A from 25 parts to 12.5 parts, and altering the amount of the dilution water from 14 parts to 26.5 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 6

With the exceptions of altering the amount of the polyether-modified organopolysiloxane A from 25 parts to 37.5 parts, altering the amount of phase inversion water from 10 parts to 6 parts, and altering the amount of the dilution water from 14 parts to 5.5 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 7

With the exceptions of altering the amount of the anionic surfactant from 1 part to 0.2 parts, and altering the amount of the dilution water from 14 parts to 14.8 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Example 8

With the exceptions of altering the amount of the anionic surfactant from 1 part to 5 parts, and altering the amount of the dilution water from 14 parts to 10 parts, a silicone microemulsion composition and a dilute system were prepared in the same manner as the example 1. For the silicone microemulsion composition, the average particle size of the emulsion particles and the viscosity were as shown in Table 1. Further, for the dilute system, the light transmittance, the average particle size of the emulsion particles and the surface tension were as shown in Table 1, and no change in external appearance was observed even when the dilute system was left to stand for one month at room temperature.

Comparative Example 1

With the exceptions of not using the anionic surfactant, and altering the amount of the dilution water from 14 parts to 15 parts, a silicone microemulsion composition and a dilute system were prepared in the same manner as the example 1. For the silicone microemulsion composition, the average particle size of the emulsion particles and the viscosity were as shown in Table 2. Further, for the dilute system, the light transmittance, the average particle size of the emulsion particles and the surface tension were as shown in Table 2. The dilute system became cloudy when left to stand for one month at room temperature.

Comparative Example 2

With the exceptions of replacing the 25 parts of the polyether-modified organopolysiloxane A used in the example 1 with 25 parts of a polyether-modified organopolysiloxane B (average composition formula: $M_2D_{10}D^R{}_5$, wherein R represents $-(CH_2)_3O(C_2H_4O)_{10}Me$), also adding 1.88 parts of a base (triethanolamine) and 3 parts of a polyhydric alcohol (1,3-butanediol) to the carboxy-modified organopolysiloxane, and altering the amount of the dilution water from 14 parts to 9.12 parts, an attempt was made to prepare a silicone microemulsion composition in the same manner as the example 1, but phase inversion could not be achieved. This result indicates that if a polyether-modified organopolysiloxane besides the component (B) is used instead of the component (B), then a microemulsion cannot be produced.

Comparative Example 3

With the exceptions of replacing the 25 parts of the polyether-modified organopolysiloxane A (average composition formula: $M_2D^R$ wherein R represents $-(CH_2)_3O(C_2H_4O)_8Me$) from the example 1 with a mixture of 12.5 parts of an alkyl-type nonionic surfactant A (Sannonic SS70, manufactured by Sanyo Chemical Industries, Ltd.), 6.25 parts of an alkyl-type nonionic surfactant B (Sannonic SS120, manufactured by Sanyo Chemical Industries, Ltd.) and 6.25 parts of an alkyl-type nonionic surfactant C (Emulgen 104P, manufactured by Kao Corporation), also adding 2.04 parts of a base (triethanolamine) (an amount sufficient to provide 1 molar equivalent of the base per 1 molar equivalent of carboxyl groups within the carboxy-modified organopolysiloxane) and 3 parts of a polyhydric alcohol (1,3-butanediol) to the carboxy-modified organopolysiloxane, and altering the amount of the dilution water from 14 parts to 8.96 parts, a silicone microemulsion composition and a dilute system were prepared in the same manner as the example 1. For the silicone microemulsion composition, the average particle size of the emulsion particles and the viscosity were as shown in Table 2. Further, for the dilute system, the light transmittance, the average particle size of the emulsion particles and the surface tension were as shown in Table 2. No change in external appearance was observed even when the dilute system was left to stand for one month at room temperature, but the surface tension was significantly higher than that of the examples 1 to 8.

TABLE 1

| | Examples | | | | | | | |
|---|---|---|---|---|---|---|---|---|
| | 1 | 2 | 3 | 4 | 5 | 6 | 7 | 8 |
| Carboxy-modified organopolysiloxane[1] | 50 | 50 | 50 | 50 | 50 | 50 | 50 | 50 |
| Polyether-modified organopolysiloxane A[2] | 25 | 25 | 25 | 25 | 12.5 | 37.5 | 25 | 25 |
| Anionic surfactant[3] | 1 | 1 | 1 | 1 | 1 | 1 | 0.2 | 5 |
| Triethanolamine | | 1.88 | | 1.88 | | | | |
| 1,3-butanediol | | | 3 | 3 | | | | |

TABLE 1-continued

|  | Examples | | | | | | | |
|---|---|---|---|---|---|---|---|---|
|  | 1 | 2 | 3 | 4 | 5 | 6 | 7 | 8 |
| Phase inversion water | 10 | 10 | 10 | 10 | 10 | 6 | 10 | 10 |
| Dilution water | 14 | 12.12 | 11 | 9.12 | 26.5 | 5.5 | 14.8 | 10 |
| Silicone microemulsion composition | | | | | | | | |
| Particle size (nm) | 36 | 36 | 14 | 19 | 86 | 10 | 61 | 24 |
| Viscosity (mPa · s) | 5060 | 250,800 | 1,427 | 10,050 | 4,120 | 834 | 5,040 | 2,265 |
| Dilute System | | | | | | | | |
| Light transmittance (%) | 89.6 | 95.7 | 95.0 | 96.0 | 41.3 | 97.6 | 93.1 | 91.5 |
| Particle size (nm) | 31 | 24 | 26 | 17 | 79 | 13 | 23 | 30 |
| Surface tension (mN/m) | 23.2 | 24.2 | 23.2 | 25.7 | 24.5 | 22.6 | 22.9 | 24.5 |
| Stability[4] | O | O | O | O | O | O | O | O |

[1] Carboxy-modified organopolysiloxane (average composition formula: $M_2D_{280}D^R_{16}$, wherein R represents —$(CH_2)_{10}COOH$)
[2] Polyether-modified organopolysiloxane A (average composition formula: $M_2D^R$, wherein R represents —$(CH_2)_3O(C_2H_4O)_8Me$)
[3] Anionic surfactant (product name: Emal 20C, manufactured by Kao Corporation)
[4] O: no change in external appearance even when left to stand for one month at room temperature.
x: became cloudy when left to stand for one month at room temperature.

TABLE 2

|  | Comparative Examples | | |
|---|---|---|---|
|  | 1 | 2 | 3 |
| Carboxy-modified organopolysiloxane [1] | 50 | 50 | 50 |
| Polyether-modified organopolysiloxane A [2] | 25 | | |
| Polyether-modified organopolysiloxane B [3] | | 25 | |
| Alkyl-type nonionic surfactant A [4] | | | 12.5 |
| Alkyl-type nonionic surfactant B [5] | | | 6.25 |
| Alkyl-type nonionic surfactant C [6] | | | 6.25 |
| Anionic surfactant [7] | | 1 | 1 |
| Triethanolamine | | 1.88 | 2.04 |
| 1,3-butanediol | | 3 | 3 |
| Phase inversion water | 10 | 10 | 10 |
| Dilution water | 15 | 9.12 | 8.96 |
| Silicone microemulsion composition | | | |
| Particle size (nm) | 99 | —[9] | 57 |
| Viscosity (mPa · s) | 3,200 | | — |
| Dilute System | | | |
| Light transmittance (%) | 70.3 | —[9] | 94.1 |
| Particle size (nm) | 68 | | 25 |
| Surface tension (mN/m) | 22.4 | | 30.1 |
| Stability [8] | x | | O |

[1] Carboxy-modified organopolysiloxane (average composition formula: $M_2D_{280}D^R_{16}$, wherein R represents —$(CH_2)_{10}COOH$)
[2] Polyether-modified organopolysiloxane A (average composition formula: $M_2D^R$, wherein R represents —$(CH_2)_3O(C_2H_4O)_8Me$)
[3] Polyether-modified organopolysiloxane B (average composition formula: $M_2D_{10}D^R_5$, wherein R represents —$(CH_2)_3O(C_2H_4O)_{10}Me$)
[4] Alkyl-type nonionic surfactant A (Sannonic SS70, manufactured by Sanyo Chemical Industries, Ltd.)
[5] Alkyl-type nonionic surfactant B (Sannonic SS120, manufactured by Sanyo Chemical Industries, Ltd.)
[6] Alkyl-type nonionic surfactant C (Emulgen 104P, manufactured by Kao Corporation)
[7] Anionic surfactant (product name: Emal 20C, manufactured by Kao Corporation)
[8] O: no change in external appearance even when left to stand for one month at room temperature.
x: became cloudy when left to stand for one month at room temperature.
[9] no phase inversion occurred.

What is claimed is:

1. A silicone microemulsion composition comprising:
(A) 100 parts by mass of a carboxy-modified organopolysiloxane represented by a general formula [1] shown below, $$R^2—(R^1_2SiO)_m(R^2R^1SiO)_nR^1_2Si—R^2 \quad [1]$$

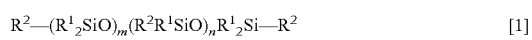

wherein each $R^1$ independently represents an unsubstituted or substituted monovalent hydrocarbon group of 1 to 20 carbon atoms, each $R^2$ independently represents $R^1$ or —$R^3$COOH, provided that at least one $R^2$ group represents —$R^3$COOH, $R^3$ represents a divalent hydrocarbon group, m represents a number of 50 to 1,000 and n represents a number of 0 to 20;
(B) 25 to 75 parts by mass of a polyether-modified organopolysiloxane represented by a general formula [2] shown below, $$R^4—(R^1_2SiO)_o(R^4R^1SiO)_pR^1_2Si—R^4 \quad [2]$$

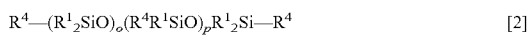

wherein $R^1$ is as defined above, each $R^4$ independently represents $R^1$ or —$(CH_2)_aO(C_2H_4O)_b(C_3H_6O)_cR^5$, provided that at least one $R^4$ group represents —$(CH_2)_aO(C_2H_4O)_b(C_3H_6O)_cR^5$, $R^5$ represents a hydrogen atom, a hydrocarbon group of 1 to 20 carbon atoms or —(CO)—$R^6$, $R^6$ represents a hydrocarbon group of 1 to 10 carbon atoms, o represents a number of 0 to 3, p represents a number of 1 to 3, a represents a number of 2 to 5, b represents a number of 5 to 15, and c represents a number of 0 to 10;
(C) 0.1 to 10 parts by mass of an anionic surfactant; and
(D) water; wherein
an average particle size of emulsion particles is not more than 100 nm.

2. The silicone microemulsion composition according to claim 1, further comprising:
(E) a base.

3. The silicone microemulsion composition according to claim 1, further comprising:
(F) a polyhydric alcohol.

4. The silicone microemulsion composition according to claim 1, wherein a dilute system comprising more than 0% by mass but not more than 10% by mass of the silicone microemulsion composition, with a remainder being water, exhibits a surface tension of not more than 30 mN/m.

5. A dilute system, comprising more than 0% by mass but not more than 10% by mass of the silicone microemulsion composition defined in claim 1, with a remainder being water, the dilute system having a surface tension of not more than 30 mN/m.

* * * * *